(12) United States Patent
Neuba et al.

(10) Patent No.: US 10,080,710 B2
(45) Date of Patent: *Sep. 25, 2018

(54) MULTI-TONAL ONE STEP DYEING WITH THICKENED PRE-TREATMENT SOLUTION

(71) Applicant: Henkel AG & Co. KGaA, Duesseldorf (DE)

(72) Inventors: Constanze Neuba, Grevenbroich (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,105

(22) Filed: Feb. 16, 2017

(65) Prior Publication Data

US 2017/0157002 A1    Jun. 8, 2017

Related U.S. Application Data

(63) Continuation of application No. PCT/EP2015/068558, filed on Aug. 12, 2015.

(30) Foreign Application Priority Data

Aug. 26, 2014    (DE) .................. 10 2014 216 940

(51) Int. Cl.

| | |
|---|---|
| *A61Q 5/10* | (2006.01) |
| *A61K 8/22* | (2006.01) |
| *A61Q 5/08* | (2006.01) |
| *A61K 8/81* | (2006.01) |
| *A61K 8/19* | (2006.01) |
| *A61K 8/42* | (2006.01) |
| *A61K 8/49* | (2006.01) |
| *A61K 8/41* | (2006.01) |
| *A61K 8/34* | (2006.01) |
| *A61K 8/23* | (2006.01) |
| *A61K 8/20* | (2006.01) |

(52) U.S. Cl.
CPC ................. *A61K 8/22* (2013.01); *A61K 8/19* (2013.01); *A61K 8/20* (2013.01); *A61K 8/23* (2013.01); *A61K 8/347* (2013.01); *A61K 8/411* (2013.01); *A61K 8/415* (2013.01); *A61K 8/42* (2013.01); *A61K 8/494* (2013.01); *A61K 8/4926* (2013.01); *A61K 8/4953* (2013.01); *A61K 8/4966* (2013.01); *A61K 8/8182* (2013.01); *A61Q 5/08* (2013.01); *A61Q 5/10* (2013.01); *A61K 2800/48* (2013.01); *A61K 2800/805* (2013.01); *A61K 2800/884* (2013.01)

(58) Field of Classification Search
CPC .......... A61K 8/22; A61K 8/8182; A61K 8/19; A61K 8/42; A61K 8/4966; A61K 8/411; A61K 8/415; A61K 8/494; A61K 8/4953; A61K 8/347; A61K 8/4926; A61K 8/23; A61K 8/20; A61K 2800/805; A61K 2800/48; A61K 2800/88; A61Q 5/08; A61Q 5/10

See application file for complete search history.

(56) References Cited

U.S. PATENT DOCUMENTS

| | | | | |
|---|---|---|---|---|
| 5,431,698 A | * | 7/1995 | Tennigkeit | A61K 8/411 8/406 |
| 9,402,795 B2 | * | 8/2016 | Neuba | A61Q 5/10 |
| 9,402,797 B2 | * | 8/2016 | Neuba | A61Q 5/10 |
| 9,445,977 B2 | * | 9/2016 | Neuba | A61K 8/411 |
| 2005/0000035 A1 | * | 1/2005 | Chan | A61K 8/22 8/405 |

FOREIGN PATENT DOCUMENTS

| | | | | |
|---|---|---|---|---|
| DE | 10037580 A1 | * | 2/2002 | ............. A61K 7/13 |
| EP | 1927340 A1 | * | 4/2008 | ............. A61Q 5/10 |
| EP | 1927340 A1 | | 6/2008 | |

OTHER PUBLICATIONS

PCT International Search Report (PCT/EP2015/068558) dated Jan. 10, 2015.
Database Chemical Abstracts Service, "Hair Dyeing Method and Pretreatment Agent for Hair Dyeing", XP002744945, Database Accession No. 159:416500, 2013.

* cited by examiner

*Primary Examiner* — Eisa B Elhilo
(74) *Attorney, Agent, or Firm* — P. Scott Smith

(57) ABSTRACT

The invention relates to a method for dyeing keratin fibers, in particular human hair, in which alter applying and allowing a thickened pre-treatment agent in the form of a lightening or bleaching agent (M1), comprising at least one oxidation agent, to react, a dye (M2) is applied directly and is allowed to react without rinsing. By carrying out said method, hair can be colored in a dyeing step and simultaneously multi-tonal dyeing with highlights is achieved.

19 Claims, No Drawings

MULTI-TONAL ONE STEP DYEING WITH THICKENED PRE-TREATMENT SOLUTION

FIELD OF THE INVENTION

The present invention relates to a method for treating keratin fibers, which allows the hair to be colored in one coloring step, while generating a multi-tonal coloration having lighter sections (strands of hair) ("highlights"). For this purpose, a thickened blonding agent in combination with an oxidative dye is used.

BACKGROUND OF THE INVENTION

Over the course of time, and in particular under the action of external conditions such as light or harmful atmospheric substances, hair loses or changes the natural color thereof and the luster or sheen thereof. Hair dyes are widely used for this reason, which are employed either in salons or as at-home use.

What are known as oxidation dyes are used for permanent, intensive colorations having appropriate fastness properties. Such dyes usually comprise oxidation dye precursors, so-called developer components and coupler components, which create the actual dyes among each other under the influence of oxidizing agents or of atmospheric oxygen. The oxidation dyes are characterized by outstanding, long lasting dyeing results. Permanent or semi-permanent coloring agents including what are known as substantive dyes (direct dyes) as the coloring component are typically used for temporary colorations.

In addition to coloring, lightening one's hair color or blonding has always been a very special desire of many consumers since a blond hair color is perceived to be attractive and desirable from a fashion point of view. When substrates are to be lightened or even bleached, the dyes coloring the substrate are typically decolorized oxidatively, using appropriate oxidizing agents, such as hydrogen peroxide.

The problem with dyeing hair, and in particular dyeing hair by way of at-home use, is that natural color nuances are completely covered, whereby multi-tonal colorations are difficult to implement.

So as to impart a more natural appearance to the hair, it is known from the prior art to partially decolorize dyed hair by deliberately applying oxidizing agents. The sections of hair ("strands") to which the oxidizing agents are applied result in bleaching at least in some proportion, resulting in a multi-tonal hair color. The oxidizing agent is applied by way of a brush, wherein the hair that is not to be treated is optionally protected from decolorization by way of an aluminum foil or what is known as a "highlighter cap."

While this kind of application solves the problem of dyeing hair as naturally as possible, a time-consuming second decolorizing step is needed, which follows the first coloring step. In particular in the case of at-home use, initially the entire hair would thus have to be colored before the user is able to add highlights. Many female consumers consider this too time-consuming, as well as frustrating, since the essential color-modifying step takes place first and is then merely "corrected" in a second step.

BRIEF SUMMARY OF THE INVENTION

It was the object of the present invention to provide a method that allows multi-tonal colorations in one coloring step. The dyeing of the hair was to accompany the generation of highlights, so that a result is directly visible after the dye has been rinsed off.

A subject matter of the present invention is thus a method for oxidatively coloring keratin fibers, wherein the method comprises the following method steps in the indicated order:
a) applying a cosmetic agent (M1) to the keratin fibers;
b) allowing the agent (M1) to act on the keratin fibers for a time period of 1 to 60 minutes;
c) applying a cosmetic agent (M2) to the keratin fibers to which the cosmetic agent (M1) has been applied;
d) allowing the cosmetic agents (M1) and (M2) to act on the keratin fibers for a time period of 1 to 70 minutes;
e) rinsing off the cosmetic agents (M1) and (M2),
characterized in that
  the cosmetic agent (M1)
  comprises at least one oxidizing agent (M1-1),
  has a pH value of 7 to 14 (M1-2), and
  does not comprise any compound from the group of the oxidation dye precursors of the developer type and the coupler type, the direct dyes, and the mixtures thereof (M1-3), and
  the cosmetic agent (M2)
  comprises at least one oxidation dye precursor of the developer type (M2-1),
  comprises at least one oxidation dye precursor of the coupler type (M2-2),
  comprises at least one oxidizing agent (M2-3), and
  has a pH value of 5 to 12 (M2-4).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that a partial pretreatment of fiber areas or strands of hair later causes these areas or strands to be colored less intensively. As a result of the pre-penetration or pretreatment of individual fiber areas or strands of hair, the dye applied immediately thereafter colors the hair in a multi-tonal manner, and a natural coloring result featuring highlights is obtained directly after the coloring step.

According to the invention, the term "keratinic fibers or keratin fibers" shall be understood to mean furs, wool, feathers, and human hair. Within the scope of the present invention, it is particularly preferred when the method according to the invention is used to color human hair.

Within the scope of the present invention, furthermore the term "thickener" shall be understood to mean compounds that are able to bind liquids, in particular water, and increase the viscosity of these liquids. Within the scope of the present invention, these also include gelling agents, which are able to thicken liquids to yield compositions having a gel-like consistency or to yield gels. According to the invention, gel-like cosmetic agents or gels shall be understood to mean dimensionally stable, easily deformable disperse systems composed of at least two components, these being the gelling agent (usually a solid, colloidally dispersed substance comprising long or heavily branched compounds) and a liquid (usually water) as the dispersant. The gelling agent forms a spatial network in the liquid, wherein the individual gel-forming compounds adhere to one another by way of primary and/or secondary valences at various spatial points.

Furthermore, the term "fatty acids," as it is used within the scope of the present invention, shall be understood to mean aliphatic carboxylic acids that include unbranched or branched carbon groups having 4 to 40 carbon atoms. The fatty acids used within the scope of the present invention can be both naturally occurring and synthetically produced fatty acids. The fatty acids can moreover be monounsaturated or polyunsaturated.

Finally, the term "fatty alcohols" within the scope of the present invention shall be understood to mean aliphatic, monohydric, primary alcohols that include unbranched or branched hydrocarbon residue having 4 to 40 carbon atoms. The fatty alcohols used within the scope of the invention may also be monounsaturated or polyunsaturated.

According to the invention, it is preferred when the method steps a) to e) are carried out in the above-listed order using a time lag between each of the individual method steps of 0 to 60 minutes, preferably of 0 to 40 minutes, and in particular 0 to 30 minutes.

In the first method step (method step a)) of the method according to the invention, a cosmetic agent (M1) is applied to the fibers. This cosmetic agent (M1), which hereafter is also referred to as the pretreatment agent or as the pre-penetration agent, is left on the keratin fibers (method step b) of the method according to the invention) for a time period of 1 minute to 60 minutes.

However, according to the invention shorter residence times of the pretreatment agent are preferred. Particularly preferred methods according to the invention are characterized in that the cosmetic agent (M1) in method step b) is allowed to act on the keratin fibers for a time period of 2 to 60 minutes, preferably of 3 to 45 minutes, and in particular of 5 to 30 minutes. By pretreating keratin fibers with the cosmetic agent (M1), ingredients of the pretreatment agent (M1) already adhere to the keratin fibers or have already penetrated into the keratin fibers in these regions, so that the dyeing result during the subsequent application of the cosmetic agent (M2) is lightened in these regions. In this way, it is possible to color the hair, and at the same time generate a multi-tonal coloration having lighter sections (strands of hair) ("highlights"), in one coloring step.

It has been shown that a pretreatment at slightly elevated temperatures causes the multi-tonal effects to appear even more vividly. Preferred methods according to the invention are characterized in that the cosmetic agent (M1) in method step b) is allowed to act at a temperature of 20° C. to 120° C., and in particular 30° C. to 120° C. Temperatures of 20° C. to 120° C., and preferably of 30° C. to 120° C., can be achieved, for example, using a hot air blow dryer or a hood dryer.

So as to generate multi-tonal colorations, the cosmetic agent (M1) should not be uniformly applied to the keratin fibers. Preferably, the cosmetic agent (M1) is applied only to individual regions, and particularly preferably only to individual strands of hair. Alternatively, the concentration of the cosmetic agent (M1) that is applied to individual strands of hair may be varied. It is also possible to initially apply the cosmetic agent (M1) uniformly to all the keratin fibers, and thereafter treat individual regions or strands of hair again with the cosmetic agent (M1). According to the invention, it is also possible to treat individual regions/strands multiple times with the cosmetic agent (M1).

In this connection, it is particularly preferred if the cosmetic agent (M1) in method step a) is only applied to individual strands of hair. According to the invention, the term "strands of hair" shall be understood to mean a portion that is separated from the totality of keratin fibers and that is composed of at least 2, preferably at least 50, and in particular at least 100 keratin fibers.

Subsequent to the residence time of the pretreatment agent, the keratin fibers are not rinsed or rubbed dry. Rather, in method step c) of the method according to the invention, a cosmetic agent (M2) is applied to the keratin fibers to which the cosmetic agent (M1) is still applied. The mixture of the cosmetic agents (M1) and (M2) created as a result of the application of the cosmetic agent (M2) to the keratin fibers is allowed to act in method step d) of the method according to the invention for a time period of 1 to 70 minutes.

According to the invention, however, shorter residence times of the cosmetic agents (M1) and (M2) in method step d) are preferred. Particularly preferred methods according to the invention are characterized in that the cosmetic agents (M1) and (M2) are allowed to act in method step d) for a time period of 1 to 60 minutes, preferably of 5 to 50 minutes, and in particular of 10 to 45 minutes.

Since the cosmetic agent (M1) in method step b) of the method according to the invention was already left on the keratin fibers for a certain amount of time, the contact of these keratin fibers with the ingredients of the cosmetic agent (M1) is longer than that with those of the cosmetic agent (M2). If the cosmetic agent (M1) was used only on individual strands of hair or in individual regions, the ingredients of the cosmetic agent (M1) are able to act more intensively in these regions, and thus weaken the action of the ingredients of the cosmetic agent (M2) in these regions, whereby a lighter coloration of these regions is achieved.

A multi-tonal color result is obtained directly after the cosmetic agents (M1) and (M2) are rinsed off in method step e) of the method according to the invention, without conducting a further step.

The cosmetic agent (M1) or the pretreatment agent is a bleaching agent, which includes at least one oxidizing agent (M1-1). Persulfates, peroxodisulfates, chlorites, hypochlorites, and in particular hydrogen peroxide and/or one of the solid addition products thereof to organic or inorganic compounds are possible oxidizing agents.

Preferred methods according to the invention are thus characterized in that the at least one oxidizing agent (M1-1) is selected from the group consisting of persulfates, peroxodisulfates, chlorites, hypochlorites, hydrogen peroxide and the solid addition products thereof to urea, melamine, polyvinylpyrrolidone and sodium borate, and the mixtures thereof.

In particularly preferred methods according to the invention, the at least one oxidizing agent (M1-1) is selected from the group consisting of hydrogen peroxide and the solid addition products thereof to urea, melamine, polyvinylpyrrolidone and sodium borate, preferably hydrogen peroxide.

So as to ensure sufficient lightening of the hair treated with the pretreatment agent, it is preferred within the scope of the present invention if the cosmetic agent (M1) comprises the at least one oxidizing agent (M1-1) in a total amount of 1.0 to 8.0 wt. %, especially 1.5 to 7.5 wt. %, preferably 2.0 to 7.0 wt. %, more preferably 2.5 to 7.0 wt. %, and in particular 3.0 to 7.0 wt. %, based on the total weight of the cosmetic agent (M1). If hydrogen peroxide and the solid addition products thereof are used as oxidizing agents, the above-mentioned total amount is calculated based on 100% H2O2.

In a further preferred embodiment, the cosmetic agent (M1) is an agent for lightening or bleaching keratin fibers, which comprises hydrogen peroxide or the solid addition products thereof to urea, melamine, polyvinylpyrrolidone and sodium borate, preferably hydrogen peroxide, as the oxidizing agent (M1-1) in a total amount of 1.0 to 12 wt. %, especially 1.5 to 12 wt. %, preferably 2.0 to 12 wt. %, more preferably 3.0 to 12 wt. %, and in particular 3.5 to 12.0 wt. %, based on the total weight of the cosmetic agent (M1). The above-mentioned total amount of hydrogen peroxide is likewise based on 100% H2O2.

So as to achieve an intensified lightening and bleaching action, the cosmetic agent (M1) can furthermore comprise at least one peroxo salt. Suitable peroxo salts are inorganic peroxo compounds, preferably selected from the group consisting of ammonium peroxodisulfate, alkali metal peroxodisulfates, ammonium peroxomonosulfates, alkali metal peroxomonosulfates, alkali metal peroxodiphospates, alkaline earth metal peroxides, and the mixtures thereof. Peroxodisulfates are particularly preferred, and in particular ammonium peroxodisulfate, potassium peroxodisulfate and sodium peroxodisulfate.

The aforementioned peroxo salts are present in a total amount of 0.5 to 20 wt. %, especially 1 to 12.5 wt. %, preferably 2.5 to 10 wt. %, and in particular 3 to 6 wt. %, based on the total weight of the cosmetic agent (M1).

The pretreatment agents (M1) used within the scope of the method according to the invention generally have an alkaline pH value, in particular between pH 7.0 and pH 14. These pH values are necessary to ensure that the outermost layer covered with scales (cuticle) opens up and allows the oxidation dye precursors to penetrate into the hair.

Preferred methods according to the invention are thus characterized in that the cosmetic agent (M1) has a pH value (M1-2) of 7.5 to 13, especially of 8.0 to 12.5, preferably of 8.0 to 12, more preferably of 8.0 to 11.5, and in particular of 8.0 to 11. These pH values can preferably be established using the alkalizing agents listed hereafter.

Organic alkalizing agents that can be used according to the invention are preferably selected from alkanolamines composed of primary, secondary or tertiary amines having a C2-C6 alkyl basic structure, which carries at least one hydroxyl group. Especially particularly preferred alkanolamines according to the invention are selected from the group consisting of 2-aminoethane-1-ol (monoethanolamine), 2-amino-2-methylpropane-1-ol and 2-amino-2-methyl-propane-1,3-diol, and the mixtures thereof. An especially preferred alkanolamine is monoethanolamine. Suitable alkaline amino acids are lysine, arginine and ornithine. Inorganic alkalizing agents according to the invention are preferably selected from the group consisting of sodium hydroxide, potassium hydroxide, calcium hydroxide, barium hydroxide, sodium phosphate, potassium phosphate, sodium silicate, potassium silicate, sodium carbonate and potassium carbonate.

Particularly preferred methods according to the invention are characterized in that the cosmetic agent (M1) comprises one or more alkalizing agents from the group consisting of sodium hydroxide, potassium hydroxide, ammonia, monoethanolamine and 2-amino-2-methylpropanol in a total amount of 0.05 to 8.0 wt. %, especially of 0.1 to 6.0 wt. %, and in particular of 0.5 to 5.0 wt. %, based on the total weight of the cosmetic agent (M1).

So as to bring out the natural and multi-tonal coloring result particularly prominently and surprisingly at the end of the method according to the invention, the pretreatment agent (M1) alone is preferably not able to be used as a separate dye. For this reason, the cosmetic agents (M1) do not comprise any compound from the group of the oxidation dye precursors of the developer type and the coupler type, the direct dyes, and the mixtures thereof (M1-3).

Preferred methods according to the invention are thus characterized in that the cosmetic agent (M1) used in method step a) comprises 0 wt. %, based on the total weight of the cosmetic agent (M1), of a compound from the group of the oxidation dye precursors of the developer type and of the coupler type, of the direct dyes, and the mixtures thereof. Within the scope of the oxidative dyeing process, oxidation dye precursors of the developer type and of the coupler type create the desired coloration by forming covalent bonds with one another solely through the use of an oxidizing agent. Direct dyes, in contrast, are dyes that attach directly to the hair and require no oxidative process, which is to say no use of an oxidizing agent, to create the color.

So as to be able to cleanly apply the pre-penetration agent (M1) in a locally delimited manner, a gel consistency of the agent has proven advantageous. The gel pretreatment agents (M1) ensure good and uniform distributability on the keratin fibers and do not cause any running or bleeding during the residence time in method step b). In this way, it is possible for the pretreatment agent (M1) to be applied to and act on limited strands of hair or regions, resulting in an outstanding multi-tonal coloring result in which the definition of strands of hair is not impaired due to running of the pretreatment agent (M1).

Thus, cosmetic agents (M1) having a dynamic viscosity of 5,000 to 90,000 mPa*s, especially of 6,000 to 80,000 mPa*s, preferably of 8,000 to 70,000 mPa*s, more preferably of 9,000 to 60,000 mPa*s, and in particular of 10,000 to 50,000 mPa*s, each measured by way of Brookfield RDV II+, spindle no. 4, 4 rpm, 20° C., are particularly preferred.

So as to establish the above-described viscosity, in particular thickeners, fatty alcohols, fatty acids saponified with alkalizing agents, and the mixtures thereof are used. Preferred methods within the scope of the present invention are thus characterized in that the cosmetic agent (M1) additionally comprises at least one viscosity-increasing compound from the group consisting of the thickeners, the fatty alcohols, the fatty acids saponified with alkalizing agents, and the mixtures thereof. The term "viscosity-increasing compounds" shall be understood to mean compounds that, when added to the cosmetic agent (M1), result in an increase in the viscosity of this agent. Furthermore, the term "fatty acids saponified with alkalizing agents" shall be understood to mean salty compounds in which the fatty acid is present as an anion and the alkalizing agent as a cation.

If thickeners are used to establish the above-described viscosity, these are preferably selected from the group consisting of thickening polysaccharides, thickening synthetic polymers, thickening inorganic compounds, and the mixtures thereof.

In this connection, it may be provided that the thickening polysaccharide is selected from the group consisting of xanthan gum, celluloses, cellulose derivatives, curdlan, algins, alginates, glucans, pullulans, amyloses, tragacanth, karaya gum, ghatti gum, agar, carrageenan, chitin, chitosan, gum arabic, gellan gum, guar gum, locust bean gum, and the mixtures thereof, preferably xanthan gum, celluloses, cellulose derivatives, and the mixtures thereof.

Within the scope of the present embodiment, it may furthermore be provided that the thickening synthetic polymer is selected from the group consisting of cross-linked homopolymers or copolymers of acrylic acid, methacrylic acid and the salts and alkyl esters thereof, homopolymers or copolymers of acrylic acid amides and/or methacrylic acid amides, copolymers of acrylic acid and acrylic acid amides and the mixtures thereof, preferably cross-linked homopolymers or copolymers of acrylic acid, methacrylic acid and the salts and alkyl esters thereof, cross-linked copolymers of ethoxylated alkyl esters of methacrylic acid and of the sulfonated acrylic acid amides and the salts thereof, and cross-linked copolymers of methacrylic acid, acrylic acid amides and of the sulfonated acrylic acid amides and the salts thereof. Such polymers are, for example, the cross-linked copolymer known under the INCI name Ammonium Acryloyldimethyltaurate/Beheneth-25 methacrylate Crosspolymer (trade name: Aristoflex HMB; Clariant), the cross-linked copolymer known under the INCI name Acrylates/C10-30 Alkyl Acrylate Crosspolymer (trade name: Carbopol; Lubrizol) and the cross-linked copolymer known under the INCI name Polyacrylate Crosspolymer-11 (trade name: Aristoflex Velvet; Clariant).

Furthermore, it may also be provided within the scope of the present embodiment that the thickening anionic compound is selected from the group consisting of electrolytes, in particular sodium chloride and potassium chloride, phyllosilicates, magnesium aluminum silicates, optionally modified bentonites, in particular optionally modified smectites, and the mixtures thereof.

Particularly preferably used thickeners are selected from the group consisting of cellulose, cellulose derivatives, xanthan gum, cross-linked homopolymers or copolymers of acrylic acid, of methacrylic acid and the salts thereof, cross-linked copolymers of ethoxylated alkyl esters of methacrylic acid and of the sulfonated acrylic acid amides and the salts thereof, cross-linked copolymers of methacrylic acid, of acrylic acid amides and of the sulfonated acrylic acid amides and the salts thereof, and mixtures of these thickeners.

In addition to the above-described thickeners, however, it is also possible to use fatty alcohols, selected from the group consisting of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoleyl alcohol, linolenyl alcohol, eleostearyl alcohol, arachyl alcohol, gadoleyl alcohol, behenyl alcohol, erucyl alcohol, and brassidyl alcohol, and the technical mixtures thereof, which develop in the high-pressure hydrogenation of technical methyl esters based on fats and oils or aldehydes from Roelen's oxo synthesis, and as a monomer fraction in the dimerization of unsaturated fatty alcohols. Particularly preferred fatty alcohols within the scope of the present invention are selected from the group consisting of lauryl alcohol, cetyl alcohol, cetearyl alcohol, stearyl alcohol, palmoleyl alcohol, isostearyl alcohol, and the mixtures thereof.

Within the scope of the present invention, the use of fatty acids, selected from the group consisting of oleic acid, linolenic acid, palmitic acid, erucic acid, 2-hexyldodecanoic acid, 2-octyldodecanoic acid, isostearic acid and the mixtures thereof is also suitable. These fatty acids are saponified by the above-described alkalizing agents, which is to say an adduct forms between the fatty acid anion and the alkalizing agent cation. The saponification causes the cosmetic agents (M1) according to the invention to become thickened to yield the above-described desired viscosity.

Within the scope of the method according to the invention, it may moreover be particularly preferred if two different viscosity-increasing compounds of those described above are used.

So as to establish the above-described viscosity, it is preferred within the scope of the present invention if the cosmetic agent (M1) comprises the additional at least one viscosity-increasing compound in a total amount of 0.1 to 10 wt. %, especially of 0.3 to 7.5 wt. %, preferably of 0.5 to 7.0 wt. %, more preferably of 0.7 to 6.5 wt. %, and in particular of 0.8 to 6.0 wt. %, based on the total weight of the cosmetic agent (M1). The above-described amounts of the viscosity-increasing compound ensure sufficient thickening, whereby running of the pretreatment agent (M1) during the residence time in method step b), and an impaired definition of the multi-tonal coloring result caused thereby, are prevented. These amounts of the viscosity-increasing compound furthermore ensure good and uniform distributability of the pretreatment agents (M1) on the keratin fibers.

In addition to the oxidation dye precursor or precursors of the developer type and of the coupler type, the direct dye or dyes, and the thickener or thickeners, the cosmetic agent (M1) used in the method according to the invention can comprise further ingredients.

According to the invention, the cosmetic agent (M1) in addition preferably comprises at least one further compound, selected from the group consisting of (i) surfactants; (ii) glycols; (iii) silicones; (iv) complexing agents; (v) cationic polymers, and (vi) the mixtures thereof.

Surfactants within the meaning of the present invention are amphiphilic (bifunctional) compounds, which are composed of at least one hydrophobic molecule part and at least one hydrophilic molecule part. A basic property of the surfactants and emulsifiers is the oriented absorption at interfaces, the aggregation into micelles, and the formation of lyotropic phases.

Surfactants that can be used within the scope of the present invention are selected from the group consisting of non-ionic surfactants, anionic surfactants, amphoteric surfactants, zwitterionic surfactants, cationic surfactants, and the mixtures thereof.

It is particularly preferred according to the invention if cosmetic agents (M1) are used in the method according to the invention which in addition comprise at least one anionic surfactant from the group of the alkyl sulfates, alkyl ether sulfates having 1 to 20, and in particular 1 to 10, oxyethylene groups, ether carboxylic acids having 10 to 20 carton atoms in the alkyl group and up to 16 glycol ether groups in the molecule, and the mixtures thereof.

Particularly preferred methods according to the invention are thus characterized in that the cosmetic agents (M1) in addition comprise at least one anionic surfactant from the group of alkyl ether sulfates having 1 to 20, and in particular 1 to 10, oxyethylene groups in a total amount of 0.1 to 10 wt. %, preferably of 0.5 to 8.0 wt. %, and in particular of 0.8 to 5.0 wt. %, based on the total weight of the cosmetic agent (M1).

Furthermore, cosmetic agents (M1) that in addition comprise at least one cationic surfactant from the group consisting of the quaternary ammonium compounds, the esterquats, the amidoamines, and the mixtures thereof, are particularly preferably used in the method according to the invention.

Particularly preferred methods according to the invention are thus characterized in that the cosmetic agents (M1) in addition comprise at least one cationic surfactant from the group consisting of alkyl trimethylammonium chlorides, dialkyldimethylammonium chlorides and trialkylmethylammonium chlorides in a total amount of 0.01 to 5.0 wt. %, preferably of 0.05 to 3.0 wt. %, and in particular of 0.1 to 1.5 wt. %, based on the total weight of the cosmetic agent (M1).

Moreover, cosmetic agents (M1) that in addition comprise at least one non-ionic surfactant from the group consisting of the fatty acid monoethanolamides, the addition products of 5 to 60 moles, and in particular 20 to 40 moles, of ethylene oxide to castor oil and hydrogenated castor oil, the ethoxylated glyceryl carboxylic acid esters having a degree of ethoxylation of 2 to 20, the alkyl oligoglucosides having 8 to 16 carbon atoms in the alkyl group, and the mixtures thereof, are particularly preferably used in the method according to the invention.

Particularly preferred methods according to the invention are thus characterized in that the cosmetic agents (M1) additionally comprise at least one non-ionic surfactant from the group of fatty acid monoethanolamides, and in particular N-(2-hydroxyethyl)-coconut fatty acid amide, in a total amount of 0.01 to 6.0 wt. %, especially 0.5 to 4.5 wt. %, and in particular of 1.0 to 3.5 wt. %, based on the total weight of the cosmetic agent (M1).

Moreover, it is likewise possible for the pretreatment agents (M1) to additionally comprise at least one zwitterionic and/or amphoteric surfactant. Preferred zwitterionic surfactants are betaines, N-alkyl-N,N-dimethylammonium glycinates, N-acyl-aminopropyl-N,N-di-methylammonium glycinates, and 2-alkyl-3-carboxymethyl-3-hydroxyethyl imidazolines. A particularly preferred zwitterionic surfactant is known under the INCI name Cocamidopropyl Betaine. Preferred amphoteric surfactants are N-alkyl glycines, N-alkyl propionic acids, N-alkyl aminobutyric acids, N-alkyl iminodipropionic acids, N-hydroxyethyl-N-alkylamidopropyl glycines, N-alkyl taurines, N-alkyl sarcosines, 2-alkyl aminopropionic acids and alkyl aminoacetic acids Particularly preferred amphoteric surfactants are N-coco alkyl aminopropionate, coco acyl aminoethylaminopropionate and C12-C18 acyl sarcosine. The zwitterionic and/or amphoteric surfactants are used in a total amount of 0.1 to 45 wt. %, preferably of 1 to 30 wt. %, and in particular of 1 to 15 wt. %, based on the total weight of the cosmetic agent (M1).

The pretreatment agents (M1) may additionally comprises at least one compound from the group of the glycols. According to the invention, the term "glycols" shall be understood to mean compounds that comprise 2 hydroxyl groups.

Suitable glycols according to the invention are selected from the group consisting of ethylene glycol, propylene glycol, (1,2-propanediol), ethylene glycol monomethyl ether, trimethylene glycol, triethylene glycol, polyethylene glycol, neopentyl glycol, and the mixtures thereof.

Particularly preferred methods according to the invention are characterized in that the cosmetic agents (M1) additionally comprise at least one glycol from the group consisting of ethylene glycol, propylene glycol, (1,2-propanediol), polyethylene glycol, and the mixtures thereof, in a total amount of 0.1 to 10 wt. %, preferably of 0.5 to 5 wt. %, and in particular of 0.8 to 3 wt. %, based on the total weight of the cosmetic agent (M1).

The cosmetic agents (M1) used in method step a) can furthermore comprise at least one silicone. A person skilled in the art considers the term "silicones" to cover a variety of structures of organosilicon compounds.

The silicones can preferably be selected from at least one representative of the group of organosilicon compounds, which is formed of:
(i) polyalkylsiloxanes, polyarylsiloxanes, polyalkylarylsiloxanes, which are volatile or non-volatile, straight-chain, branched or cyclic, cross-linked or not cross-linked;
(ii) polysiloxanes, which, in the general structure thereof, include one or more organofunctional groups, which are selected from:
   a. substituted or unsubstituted aminated groups;
   b. (per)fluorinated groups;
   c. thiol groups;
   d. carboxylate groups;
   e. hydroxylated groups;
   f. alkoxylated groups;
   g. acyloxyalkyl groups;
   h. amphoteric groups;
   i. bisulfite groups;
   j. hydroxyacylamino groups;
   k. carboxy groups;
   l. sulfonic acid groups; and
   m. sulfate or thiosulfate groups;
(iii) linear polysiloxane(A)/polyoxyalkylene(B) block copolymers of the (A-B)n type where n>3;
(iv) grafted silicone polymers having a non-silicone-containing, organic skeleton, which are composed of an organic main chain formed of organic monomers that do not include any silicone, onto which at least one polysiloxane macromer was grafted in the chain and optionally on at least one chain end;
(v) grafted silicone polymers having a polysiloxane skeleton onto which non-silicone-containing, organic monomers were grafted that include a polysiloxane main chain, onto which at least one organic macromer that does not include silicone was grafted in the chain and optionally on at least one of the ends thereof, such as the commercial product Abil B 8832 from Degussa sold under the INCI name Bis-PEG/PPG-20/20 Dimethicone;
(vi) or the mixtures thereof.

Particularly preferred methods according to the invention are characterized in that the cosmetic agents (M1) additionally comprise at least one silicone selected from the group consisting of dimethicones, amodimethicones, dimethiconols, and the mixtures thereof, in a total amount of 0.001 to 2.0 wt. %, preferably of 0.005 to 1.5 wt. %, and in particular of 0.01 to 0.5 wt. %, based on the total weight of the cosmetic agent (M1).

It has proven advantageous if the cosmetic agents (M1) used according to the invention additionally comprise at least one stabilizer or complexing agent so as to stabilize the oxidizing agent, and in particular the hydrogen peroxide.

Particularly preferred methods according to the invention are thus characterized in that the cosmetic agents (M1) comprise stabilizers or complexing agents from the group consisting of EDTA and EDDS, phosphonates, in particular 1-hydroxyethane-1,1-diphosphonic acid (HEDP) and/or ethylenediamine tetramethylene phosphonate (EDTMP) and/or diethylenetriamine pentamethylene phosphonate (DTPMP) and the sodium salts thereof, and the mixtures thereof, in a total amount of 0.001 to 5.0 wt. %, especially of 0.005 to 2.5 wt. %, preferably of 0.01 to 1.5 wt. %, and in particular of 0.05 to 1.0 wt. %, based on the total weight of the cosmetic agent (M1).

Within the scope of the present invention, it has furthermore proven advantageous when the cosmetic agents (M1) comprise at least one cationic polymer. Cationic polymers that are suitable according to the invention shall be understood to mean polymers that comprise "temporarily cationic" or "permanently cationic" groups in the main chain and/or side chain. According to the invention, polymers that comprise a cationic group, regardless of the pH value of the agent, are referred to as "permanently cationic." These are generally polymers that include a quaternary nitrogen atom, for example in the form of an ammonium group.

Preferred cationic groups comprise quaternary ammonium groups. In particular, those homopolymers and copolymers in which the quaternary ammonium group is bound via a C1-4 hydrocarbon group to a polymer main chain composed of acrylic acid, methacrylic acid or the derivatives thereof have proven to be particularly suitable. Such homopolymers and copolymers are commercially available, for example, under the trade names Salcare® SC 95, Salcare® SC 96 and Salcare® SC 92.

It is likewise possible to use the polymers known under the designations Polyquaternium-2, Polyquaternium-8, Polyquaternium-17, Polyquaternium-24 (commercial product, such as Quatrisoft® LM 200), Polyquaternium-27 and Polyquaternium-87 as cationic polymers.

Particularly preferred methods according to the invention are characterized in that the cosmetic agents (M1) comprise at least one cationic polymer from the group consisting of Polyquaternium-2, Polyquaternium-8, Polyquaternium-17, Polyquaternium-24, Polyquaternium-27 and Polyquaternium-87 in a total amount of 0.1 to 5.0 wt. %, preferably of 0.2 to 3.0 wt. %, and in particular of 0.5 to 2.0 wt. %, based on the total weight of the cosmetic agent (M1).

So as to prevent a premature, undesirable reaction of the ingredients or a premature decomposition of the oxidizing agent in an alkaline environment, oxidizing agents and alkalizing agents are advantageously formulated separately from one another and brought in contact only immediately prior to use. Lightening or bleaching agents are thus usually offered in the form of a kit (multi-component packaging unit) comprising two components, wherein the first component includes the oxidizing agent and the second component includes the alkalizing agent (such as ammonia).

In a further embodiment of the present invention, preferred cosmetic agents (M1) are thus those that are characterized by being prepared immediately prior to use by mixing at least two preparations, wherein the at least two preparations are provided in at least two separately formulated containers, and wherein one container comprises an oxidizing agent preparation (M1a) including at least one oxidizing agent, and a further container comprises an alkalizing agent preparation (M1b), which includes at least one alkalizing agent in a cosmetically compatible carrier.

The oxidizing agent preparation (M1a) preferably comprises the oxidizing agents listed in connection with the cosmetic agent (M1) in the form of hydrogen peroxide and/or one of the solid addition products thereof to organic or inorganic compounds, such as urea, melamine and sodium borate, and optionally at least one active ingredient, auxiliary substance or additive listed above in connection with the cosmetic agent (M1).

It has proven advantageous if the oxidizing agent preparations (M1a) additionally comprise at least one abovementioned stabilizer or complexing agent so as to stabilize the oxidizing agent, and in particular the hydrogen peroxide. Particularly preferred stabilizers are in particular EDTA and EDDS, as well as phosphonates, in particular 1-hydroxyethane-1,1-diphosphonic acid (HEDP) and/or ethylenediamine tetramethylene phosphonate (EDTMP) and/or diethylenetriamine pentamethylene phosphonate (DTPMP), or the sodium salts thereof.

The alkalizing agent preparation (M1b) preferably includes the alkalizing agents listed in connection with the cosmetic agent (M1) in the form of sodium hydroxide, potassium hydroxide, ammonia, monoethanolamine and 2-amino-2-methylpropanol, and optionally at least one active ingredient, auxiliary substance or additive listed above in connection with the cosmetic agent (M1). According to the invention, the alkalizing agent in the alkalizing agent preparation (M1b) is thus particularly preferably selected from the group consisting of sodium hydroxide, potassium hydroxide, ammonia, monoethanolamine and 2-amino-2-methylpropane, and the mixtures thereof, and is present in a total amount of 0.2 to 9.0 wt. %, especially of 0.3 to 8.0 wt. %, preferably of 0.4 to 7.0 wt. %, and in particular of 0.5 to 6.5 wt. %, based on the total weight of the alkalizing agent preparation (M1b).

In method step c) of the method according to the invention, a cosmetic agent (M2) is applied to the keratin fibers, to which the agent (M1) is still applied. This cosmetic agent (M2), which hereafter is also referred to as a dye, comprises at least one oxidizing dye precursor of the developer type (M2-1), at least one oxidation dye precursor of the coupler type (M2-2), and at least one oxidizing agent (M2-3).

Preferred cosmetic agents (M2) comprise at least one oxidation dye precursor of the developer type. Corresponding methods according to the invention, in which the cosmetic agent (M2), serving as an oxidation dye precursor (M2-1), comprises one or more oxidation dye precursors of the developer type, are preferred according to the invention. According to the invention, the at least one oxidation dye precursor of the developer type (M2-1) is preferably selected from the group consisting of 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazole-1-on, p-phenylenediamin, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazole-1-yl)propyl]amine, bis-(2-hydroxy-5-aminophenyl)methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, and the physiologically compatible salts thereof, and the mixtures thereof.

So as to obtain natural colorations, usually multiple oxidation dye precursors of the developer type can be used. Preferred cosmetic agents (M2) are thus characterized in that the at least one oxidation dye precursor of the developer type (M2-1) is selected from at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis-(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazole-1-yl)propyl]amine; p-toluylenediamine/bis-(2-hydroxy-5-aminophenyl)methane; p-toluylenediamine/4-amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis-(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methylphenyl)-N-[3-(1H-imidazole-1-yl)propyl]amine; 2-(2-hydroxyethyl)-p-phenylenediamine/bis-(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis-(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3-(1H-imidazole-1-yl)-propyl]amine; bis-(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine and/or 4-amino-3-methylphenol/4,5-diamino-1-(2-hydroxyethyl)pyrazole and/or the physiologically compatible salts thereof.

According to a particularly preferred embodiment of the first subject matter of the invention, the at least one oxidation dye precursor of the developer type (M2-1) is selected from the group consisting of p-toluylenediamine, 4-amino-3-methylphenol, 4,5-diamino-1-(2-hydroxyethyl)pyrazole, 2,4,5,6-tetraaminopyrimidine and/or the physiologically compatible salts thereof, and the mixtures thereof. It has been shown that the use of the specific oxidation dye precursors of the developer type (M2-1) in the dyes (M2) used in the scope of the method according to the invention result in particularly vivid multi-tonal colorations that are color-fast to washing, rubbing, sweating and UV radiation.

Multi-tonal colorations that have a particularly appealing appearance are obtained when the cosmetic agent (M2) comprises the least one oxidation dye precursor of the developer type (M2-1) in a total amount of 0.0025 to 10.0 wt. %, especially of 0.004 to 8.0 wt. %, preferably of 0.005 to 5.0 wt. %, and in particular 0.01 to 3.5 wt. %, based on the total weight of the cosmetic agent (M2). The above-described amounts of the developer component (M2-1) result in multi-tonal colorations that have particularly intensive and vivid colors and a high resistance to environmental conditions, such as hair washing, UV light, sweat and rubbing.

The oxidative dye (M2) comprises at least one oxidation dye precursor of the coupler type (M2-2) as a further component. Within the scope of oxidative dyeing, oxidation dye precursors of the coupler type alone do not provide any significant coloration, but require the presence of oxidation dye precursors of the developer type for sufficient coloration. Oxidation dye precursors of the coupler type within the meaning of the invention allow at least one substitution of a chemical group of the coupler by the oxidized form of the developer component. As a result, a covalent bond forms between the coupler component and the developer component.

Within the scope of the present invention, it is preferred for the at least one oxidation dye precursor of the coupler type (M2-2) to be selected from the group consisting of m-aminophenol and the derivatives thereof, o-aminophenol and the derivatives thereof, m-diaminobenzene and the derivatives thereof, o-diaminobenzene and the derivatives thereof, dihydroxybenzene and trihydroxybenzene derivatives, pyridine derivatives, naphthalene derivatives, morpholine derivatives, quinoxaline derivatives, pyrazole derivatives, indole derivatives, pyrimidine derivatives, methylenedioxybenzene derivatives and/or the physiologically compatible salts thereof, and the mixtures thereof.

Preferred methods according to the invention are characterized in that the at least one oxidation dye precursor of the coupler type (M2-2) is selected from the group consisting of resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, 1-naphthol and/or the physiologically compatible salts thereof, and the mixtures thereof. The above-described coupler components (M2-2), in combination with the at least one developer component (M2-1), in the oxidative dye (M2) result in particularly intensive and long-lasting multi-tonal coloring results.

According to the invention, the cosmetic agent (M2) preferably comprises the at least one oxidation dye precursor of the coupler type (M2-2) in a total amount of 0.0001 to 6.0 wt. %, especially 0.001 to 5.5 wt. %, preferably 0.002 to 4.5 wt. %, in particular of 0.005 to 2.5 wt. %, and in particular of 0.01 to 2.0 wt. %, based on the total weight of the cosmetic agent (M2). The above-described amounts of the coupler component (M2-2) in the oxidative dyes (M2) used within the scope of the method according to the invention result in particularly vivid multi-tonal colorations that are color-fast to washing, rubbing, sweating and UV radiation.

So as to ensure balanced and subtle nuancing, the oxidative dyes (M2) used within the scope of the method according to the invention can additionally comprise at least one direct dye. Direct dyes are dyes that attach directly to the hair and require no oxidative process to develop the color. Direct dyes are usually nitrophenylene diamines, nitroaminophenols, azo dyes, anthraquinones or indophenols.

According to a preferred embodiment of the first subject matter of the invention, the at least one direct dye (M2) is selected from the group consisting of anionic direct dyes, cationic direct dyes, non-ionic direct dyes, and the mixtures thereof.

In this connection, it may be provided according to the invention that the anionic direct dye is selected from the group consisting of Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, tetrabromophenol blue and/or the physiologically compatible salts thereof.

Within the scope of the present embodiment, it may furthermore be provided that the cationic direct dye is selected from the group consisting of Basic Blue 7, Basic Blue 26, Basic Violet 2 and Basic Violet 14, Basic Yellow 57, Basic Red 76, Basic Blue 99, Basic Brown 16 and Basic Brown 17, HC Blue 16, Basic Yellow 87, Basic Orange 31 and Basic Red 51, and/or the physiologically compatible salts thereof.

Moreover, it may be provided within the scope of the present embodiment that the non-ionic direct dye is selected from the group consisting of HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid, 2-amino-6-chloro-4-nitrophenol, 4-ethylamino-3-nitrobenzoic acid and 2-chloro-6-ethylamino-4-nitrophenol, and/or the physiologically compatible salts thereof, preferably 2-amino-6-chloro-4-nitrophenol and/or 4-amino-3-nitrophenol and/or the physiologically compatible salts thereof.

Oxidative dyes (M2) that are particularly preferably used within the scope of the method according to the invention additionally comprise at least one direct dye, which is selected from the group consisting of 2-amino-6-chloro-4-nitrophenol, HC Blue 12, HC Yellow 2, HC Violet 14D and/or the physiologically compatible salts thereof, and the mixtures thereof. When these specific direct dyes are used, particularly balanced and subtle nuancing is achieved during the method according to the invention or during the multi-tonal coloration.

According to the invention, the cosmetic agent (M2) in addition preferably comprises at least one direct dye in a total amount of 0.00001 to 5.0 wt. %, especially of 0.00005 to 4.5 wt. %, preferably of 0.0001 to 4.0 wt. %, more preferably of 0.0005 to 3.5 wt. %, and in particular of 0.001 to 3.0 wt. %, based on the total weight of the cosmetic agent (M2). The above-described amounts of the direct dyes result in particularly balanced nuances within the scope of the multi-tonal coloration according to the method according to the invention.

The cosmetic agent (M2) can also comprise at least one alkalizing agent. Suitable alkalizing agents and the total amounts thereof that can be used have already been described in connection with the pretreatment agent (M1). It is necessary to establish an alkaline pH value using the at least one alkalizing agent so as to ensure that the outermost layer covered with scales (cuticle) opens up and allows the oxidation dye precursors to penetrate into the hair.

Preferred methods according to the invention are thus characterized in that the cosmetic agent (M2) has a pH value of 5.0 to 12, especially of 5.0 to 11, preferably of 5.5 to 10, and in particular of 6.0 to 9.0.

Particularly vivid multi-tonal colorations are achieved, when the sequentially applied cosmetic agents (M1) and (M2) have differing pH values. Thus, methods according to the invention in which the cosmetic agent (M1) and the cosmetic agent (M2) have differing pH values are preferred.

The dyes (M2) may comprise additional active ingredients, auxiliary substances and additives so as to improve the coloring performance and establish further desired properties of the cosmetic agents (M2).

It is thus preferred according to the invention if the cosmetic agent (M2) additionally comprises at least one further compound, selected from the group consisting of (i) thickeners; (ii) surfactants; (iii) cationic polymers; (iv) silicones; (v) alkalizing agents; and (v) the mixtures thereof.

It has proven advantageous when the cosmetic agents (M2) likewise comprise at least one thickener. There are no general restrictions with respect to these thickeners. Suitable thickeners are the compounds described in connection with the pretreatment agent (M1), which can likewise be used to thicken the dyes (M2). In addition, it is also possible to use the organic and inorganic compounds listed hereafter.

Suitable thickeners are anionic synthetic polymers, cationic synthetic polymers, and non-ionic synthetic polymers, such as polyvinyl alcohol or polyvinylpyrrolidone.

The cosmetic agents (M2) used in the method according to the invention can also comprise zwitterionic polymers as thickeners, which are selected from the following group:
  copolymers of dimethyldiallylammonium salts and acrylic acid, such as Polyquaternium-22;
  copolymers of dimethyldiallylammonium salts and methacrylic acid;
  copolymers of N,N,N-trimethyl-3-[(2-methyl-1-oxo-2-propene-1-yl)amino]-1-propanaminium salts and acrylic acid;
  copolymers of N,N,N-trimethyl-3-[(2-methyl-1-oxo-2-propene-1-yl)amino]-1-propanaminium salts and methacrylic acid;
  copolymers of N,N,N-trimethyl-2-[(2-methyl-1-oxo-2-propene-1-yl)amino]-1-ethanaminium salts and acrylic acid;
  copolymers of N,N,N-trimethyl-2-[(2-methyl-1-oxo-2-propene-1-yl)amino]-1-ethanaminium salts and methacrylic acid;
  copolymers of N,N,N-trimethyl-3-[(2-methyl-1-oxo-2-propene-1-yl)amino]-1-propanaminium salts, acrylic acid, and acrylamide, such as Polyquaternium-53;
  copolymers of N,N,N-trimethyl-3-[(2-methyl-1-oxo-2-propene-1-yl)amino]-1-propanaminium salts, methacrylic acid and acrylamide;
  copolymers of 1-ethenyl-3-methyl-1H-imidazolium salts, 1-ethenyl-1H-imidazole, 1-ethenyl-2-pyrrolidinone and methacrylic acid, such as Polyquaternium-86;
  copolymers of 1-ethenyl-3-methyl-1H-imidazolium salts, 1-ethenyl-1H-imidazole, 1-ethenyl-2-pyrrolidinone and acrylic acid.
  It is also possible to use mixtures of the aforementioned zwitterionic polymers to thicken the cosmetic agents (M2).

The dyes (M2) are preferably provided as a liquid preparation, and a surface-active substance is therefore also added to these agents, wherein, depending on the field of application, such surface-active substances are referred to as surfactants or as emulsifiers. They are preferably selected from anionic, cationic, zwitterionic, amphoteric and non-ionic surfactants and emulsifiers.

Within the scope of the present embodiment, it may be provided that the anionic surfactant is selected from the group of alkyl sulfates and alkyl polyglycol ether sulfates of formula R2-O(CH2-CH2O)x-OSO3H, in which R2 is a linear alkyl group having 8 to 30 carbon atoms, and x=0 or 1 to 12, salts of linear and branched carboxylic acids having 8 to 30 carbon atoms, ether carboxylic acids of formula R3-O—(CH2-CH2O)x-CH2-COOH, in which R3 is a linear alkyl group having 8 to 30 carbon atoms, and x=0 or 1 to 16, and the mixtures thereof. The anionic surfactants are preferably used in a total amount of 0.1 to 45 wt. %, preferably of 1 to 30 wt. %, and in particular of 1 to 15 wt. %, based on the total amount of the cosmetic agent (M2).

In this connection, it may furthermore be provided according to the invention that the non-ionic surfactant is selected from the group consisting of ethoxylated alcohols and carboxylic acids having 8 to 13 carbon atoms and 2 to 30 ethylene oxide units, addition products of 5 to 60 moles ethylene oxide to castor oil and hydrogenated castor oil, alkyl polyglucosides of formula R1O-[G]p, in which R1 denotes an alkyl residue and/or an alkenyl residue having 4 to 22 carbon atoms, G denotes a sugar residue having 5 or 6 carbon atoms, and p denotes numbers from 1 to 10, monoethanolamides of carboxylic acids having 8 to 30 carbon atoms, and the mixtures thereof.

Moreover, it may also be provided within the scope of the present embodiment that the amphoteric surfactant is selected from the group consisting of amphoacetates comprising carboxylic acid groups having 8 to 30 carbon atoms, N-alkylglycines, N-alkylpropionic acids, N-alkylamidobutyric acids, N-alkyliminodipropionic acids, N-hydroxyethyl-N-alkylamidopropylglycines, N-alkyl taurines, N-alkyl sarcosines, 2-alkylaminopropionic acids, alkylaminoacetic acids, and the mixtures thereof.

Within the scope of the present embodiment, it may furthermore be provided that the zwitterionic surfactant is selected from the group consisting of betaines, N-alkyl-N, N-dimethylammonium glycinates, N-acyl-amidopropyl-N, N-dimethylammonium glycinates, 2-alkyl-3-carboxymethyl-3-hydroxyethyl imidazolines, and the mixtures thereof.

The non-ionic and/or zwitterionic and/or amphoteric surfactants are preferably used in a total amount of 0.1 to 45 wt. %, preferably of 1 to 30 wt. %, and in particular of 1 to 15 wt. %, based on the total amount of the cosmetic agent (M2).

Moreover, the use of cationic surfactants, cationic polymers, and silicones in the cosmetic agent (M2) may be provided. Suitable cationic surfactants, cationic polymers and silicones, as well as the total amounts present in the cosmetic agents (M2), have already been described in connection with the pretreatment agent (M1).

The cosmetic agent (M2) can also comprise at least one alkalizing agent. Suitable alkalizing agents and the total amounts thereof that can be used have already been described in connection with the pretreatment agent (M1). The alkalizing agent is particularly preferably selected from the group consisting of sodium hydroxide, potassium hydroxide, ammonia, monoethanolamine and 2-amino-2-methylpropane, and the mixtures thereof, and is present in a total amount of 0.05 to 8.0 wt. %, especially of 0.1 to 6.0 wt. %, preferably of 0.3 to 5.5 wt. %, and in particular of 0.5 to 5.0 wt. %, based on the total weight of the cosmetic agent (M2). It is necessary to establish an alkaline pH value using the at least one alkalizing agent so as to ensure that the outermost layer covered with scales (cuticle) opens up and allows the oxidation dye precursors to penetrate into the hair.

The oxidation dye precursors (developer and coupler) themselves are not dyed. The actual dyes are not formed until later during the course of the application as a result of the contact of the oxidation dye precursors with an oxidizing agent (preferably hydrogen peroxide). In a chemical reaction, the developers used as oxidation dye precursors (such as p-phenylenediamine derivatives or p-aminophenol derivatives) are initially oxidatively converted by way of hydrogen peroxide into a reactive intermediate, also referred to as quinonimine or quinone diimine, which then reacts with the couplers in an oxidative coupling reaction to yield the respective dye.

The cosmetic agents (M2) thus additionally comprise one or more oxidizing agents (M2-3). Persulfates, peroxodisulfates, chlorites, hypochlorites, and in particular hydrogen peroxide and/or one of the solid addition products thereof to organic or inorganic compounds are possible oxidizing agents.

Preferred methods according to the invention are thus characterized in that the cosmetic agent (M2) comprises at least one oxidizing agent (M2-3) from the group consisting of persulfates, peroxodisulfates, chlorites, hypochlorites, hydrogen peroxide and the solid addition products thereof to urea, melamine, polyvinylpyrrolidone and sodium borate, preferably hydrogen peroxide, in a total amount of 0.1 to 6 wt. %, preferably of 0.3 to 4 wt. %, and in particular of 0.5 to 3 wt. %, based on the total weight of the cosmetic agent (M2). If hydrogen peroxide and the solid addition products thereof are used as oxidizing agents, the above-mentioned total amount is calculated based on 100% H2O2.

In a further preferred embodiment, the cosmetic agent (M2) is an agent for dyeing, and optionally simultaneously for lightening, keratin fibers, which comprises hydrogen peroxide in a total amount of 0.5 to 15 wt. %, especially 1.0 to 12.5 wt. %, preferably 1.5 to 10 wt. %, and in particular 2.0 to 6.5 wt. %, based on the total weight of the cosmetic agent (M2). The above-mentioned total amount of hydrogen peroxide is based on 100% H2O2.

So as to achieve an intensified lightening and bleaching action, the cosmetic agent (M2) can furthermore comprise at least one peroxo salt. Suitable peroxo salts are inorganic peroxo compounds, preferably selected from the group consisting of ammonium peroxodisulfate, alkali metal peroxodisulfates, ammonium peroxomonosulfates, alkali metal peroxomonosulfates, alkali metal peroxodiphospates, alkaline earth metal peroxides, and the mixtures thereof. Peroxodisulfates are particularly preferred, and in particular ammonium peroxodisulfate, potassium peroxodisulfate and sodium peroxodisulfate.

The aforementioned peroxo salts are present in a total amount of 0.5 to 20 wt. %, especially 1 to 12.5 wt. %, preferably 2.5 to 10 wt. %, and in particular 3 to 6 wt. %, based on the total weight of the cosmetic agent (M2).

The lightening or bleaching agent (M1) preferably comprises the oxidizing agent (M1-1) in a higher total substance amount than the cosmetic agent (M2). This results in particularly intensive and vivid multi-tonal colorations, which moreover have a high resistance to environmental conditions, such as hair washing, sweat, UV light, or rubbing.

According to a particularly preferred embodiment of the present invention, the quantity ratio of the total amount of the oxidizing agent (M1-1) in the cosmetic agent (M1) to the total amount of the oxidizing agent (M2-3) in the cosmetic agent (M2) thus has a value (M1-1)/(M2-3) of 16:1 to 1:1, especially of 8:1 to 1:1, preferably of 6:1 to 1:1, more preferably of 5:1 to 1:1, and in particular of 4:1 to 1:1.

So as to prevent a premature, undesirable reaction of the oxidation dye precursors by the oxidizing agent, the oxidation dye precursors and alkalizing agents themselves are advantageously formulated separately from one another and brought in contact only immediately prior to use. Oxidative dyes are thus usually offered in the form of a kit (multi-component packaging unit) comprising two components, wherein the first component includes the oxidation dye precursors, and optionally direct dyes and an alkalizing agent (such as ammonia), and the second component includes the oxidizing agent.

In a further embodiment of the present invention, preferred cosmetic agents (M2) are thus those that are characterized by being prepared immediately prior to use by mixing at least two preparations, wherein the at least two preparations are provided in at least two separately formulated containers, and wherein one container includes a dye (M2a), which comprises at least one oxidation dye precursor in a cosmetic carrier, and a further container includes an oxidizing agent preparation (M2b), comprising at least one oxidizing agent.

The dye (M2a) preferably comprises the oxidation dye precursors of the developer type and/or of the coupler type described above in connection with the cosmetic agent (M2), optionally at least one direct dye, and optionally at least one active ingredient, auxiliary substance or additive listed above in connection with the cosmetic agent (M2). The oxidizing agent preparation (M2b) preferably comprises an oxidizing agent in the form of hydrogen peroxide and/or one of the solid addition products thereof to organic or inorganic compounds, such as urea, melamine and sodium borate.

Such oxidizing agent preparations (M2b) are preferably aqueous, flowable oxidizing agent preparations. Preferred preparations (M2b) are characterized in that the flowable oxidizing agent preparation (M2b) comprises 40 to 90 wt. %, especially 50 to 90 wt. %, preferably 55 to 89 wt. %, more preferably 60 to 87 wt. %, and in particular 65 to 85 wt. % water, based on the total weight of the oxidizing agent preparation (M2b).

The total amount of oxidizing agent, and in particular of hydrogen peroxide, in the oxidizing agent preparation (M2b) is preferably 0.5 to 12 wt. %, especially 1.0 to 10 wt. %, and in particular 1.5 to 6.0 wt. %, based on the total weight of the oxidizing agent preparation (M2b). If hydrogen peroxide and the solid addition products thereof are used as oxidizing agents, the above-mentioned total amount is calculated based on 100% H2O2.

According to the invention, the oxidizing agent preparation (M2b) can also be applied to the hair together with a catalyst, which activates oxidation of the dye precursors. Such catalysts are certain enzymes, iodides, quinones or metal ions, for example.

It has proven advantageous for the oxidizing agent preparations (M2b) to additionally comprise at least one stabilizer or complexing agent so as to stabilize the oxidizing agent, and in particular the hydrogen peroxide. Particularly preferred stabilizers are in particular EDTA and EDDS, as well as phosphonates, in particular 1-hydroxyethane-1,1-diphosphonic acid (HEDP) and/or ethylenediamine tetramethylene phosphonate (EDTMP) and/or diethylenetriamine pentamethylene phosphonate (DTPMP), or the sodium salts thereof.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A method for oxidatively dying keratin fibers, comprising:
  a. applying a cosmetic agent (M1) to the keratin fibers;
  b. allowing the agent (M1) to act on the keratin fibers for a time period of 1 to 60 minutes;
  c. following the elapsing of the time period of 1 to 60 minutes and without rinsing or drying the keratin fibers, applying a cosmetic agent (M2) to the keratin fibers to which the cosmetic agent (M1) has been applied;
  d. allowing the cosmetic agents (M1) and (M2) to act on the keratin fibers for a time period of 1 to 70 minutes;
  e. rinsing off the cosmetic agents (M1) and (M2),
wherein,
  the cosmetic agent (M1)
    comprises at least one oxidizing agent (M1-1),
    has a pH of 7 to 14 (M1-2), and
    does not comprise any compound from the group of the oxidation dye precursors of the developer type and the coupler type, the direct dyes, and the mixtures thereof (M1-3), and
  the cosmetic agent (M2)
    comprises at least one oxidation dye precursor of the developer type (M2-1),
    comprises at least one oxidation dye precursor of the coupler type (M2-2),
    comprises at least one oxidizing agent (M2-3), and
    has a pH value of 5 to 12 (M2-4).

2. The method according to claim 1, wherein cosmetic agent (M1) in method step b) is allowed to act on the keratin fibers for a time period of 2 to 60 minutes.

3. The method according to claim 1, wherein the cosmetic agent (M1) in method step b) is allowed to act on the keratin fibers for a time of 5 to 30 minutes.

4. The method according to claim 1, wherein the cosmetic agent (M1) is only applied to individual strands of hair in method step a).

5. The method according to claim 1, wherein the cosmetic agents (M1) and (M2) are allowed to act in method step d) for a time period of 1 to 60 minutes.

6. The method according to claim 1, wherein the cosmetic agents (M1) and (M2) are allowed to act in method step d) for a period of 10 to 45 minutes.

7. The method according to claim 1, wherein the cosmetic agent (M1) comprises the at least one oxidizing agent (M1-1) in a total amount of 1.0 to 8.0 wt. %, based on the total weight of the cosmetic agent (M1).

8. The method according to claim 1, wherein the cosmetic agent (M1) comprises the at least one oxidizing agent (M1-1) in a total amount of 3.0 to 7.0 wt. %, based on the total weight of the cosmetic agent (M1).

9. The method according to claim 1, wherein the cosmetic agent (M1) comprises hydrogen peroxide or the solid addition products thereof with urea, melamine, polyvinylpyrrolidone and sodium borate, as the oxidizing agent (M1-1) in a total amount of 1.0 to 12 wt. %.

10. The method according to claim 1, wherein the cosmetic agent (M1) has a pH value (M1-2) of 7.5 to 13.

11. The method according to claim 1, wherein the cosmetic agent (M1) has a dynamic viscosity of 5,000 to 90,000 mPa*s measured by way of Brookfield RDV II+, spindle no. 4, 4 rpm, 20° C.

12. The method according to claim 1, wherein the at least one oxidation dye precursor of the developer type (M2-1) is selected from the group consisting of: p-toluylenediamine, 4-amino-3-methylphenol, 4,5-diamino-1-(2-hydroxyethyl)pyrazole, 2,4,5,6-tetraaminopyrimidine, the physiologically compatible salts thereof, and the mixtures thereof.

13. The method according to claim 1, wherein the cosmetic agent (M2) comprises that least one oxidation dye precursor of the developer type (M2-1) in a total amount of 0.0025 to 10.0 wt. % based on the total weight of the cosmetic agent (M2).

14. The method according to claim 1, wherein the at least one oxidation dye precursor of the coupler type (M2-2) is selected from the group consisting of: resorcinol, 2-methylresorcinol, 4-chlororesorcinol, 5-amino-2-methylphenol, 3-aminophenol, 2-(2,4-diaminophenoxy) ethanol, 1,3-bis-(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, 1-naphthol, 2-amino-4-hydroxyethylamino anisole, the physiologically compatible salts thereof, and the mixtures thereof.

15. The method according to claim 1, wherein the cosmetic agent (M2) comprises the least one oxidation dye precursor of the coupler type (M2-2) in a total amount of 0.0001 to 6.0 wt. % based on the total weight of the cosmetic agent (M2).

16. The method according to claim 1, wherein the cosmetic agent (M2) has a pH value of 5.0 to 12.

17. The method according to claim 1, wherein the cosmetic agent (M2) comprises at least one oxidizing agent (M2-3) selected from the group consisting of: persulfates, peroxodisulfates, chlorites, hypochlorites, hydrogen peroxide and the solid addition products thereof to urea, melamine, polyvinylpyrrolidone and sodium borate, in a total amount of 0.1 to 6 wt. % based on the total weight of the cosmetic agent (M2).

18. The method according to claim 1, wherein the quantity ratio of the total amount of the oxidizing agent (M1-1) in the cosmetic agent (M1) to the total amount of the oxidizing agent (M2-3) in the cosmetic agent (M2) is (M1-1)/(M2-3) of 16:1 to 1:1.

19. The method according to claim 1, wherein the quantity ratio of the total amount of the oxidizing agent (M1-1) in the cosmetic agent (M1) to the total amount of the oxidizing agent (M2-3) in the cosmetic agent M2 is 4:1 to 1:1.

* * * * *